United States Patent [19]

Hansenne-Richoux

[11] Patent Number: 5,660,853
[45] Date of Patent: Aug. 26, 1997

[54] PROCESS FOR MANUFACTURING A COSMETICS COMPOSITION FOR APPLICATION TO HAIR, COMPOSITION OBTAINED BY THIS PROCESS AND PROCESS FOR COSMETIC TREATMENT USING THE SAID COMPOSITION

[75] Inventor: Isabelle Hansenne-Richoux, Paris, France

[73] Assignee: L'Oreal, Paris, France

[21] Appl. No.: 917,304

[22] Filed: Jul. 23, 1992

[30] Foreign Application Priority Data

Jul. 24, 1991 [FR] France ................... 91 09340

[51] Int. Cl.$^6$ .................... A61K 7/00; A61K 7/07
[52] U.S. Cl. .................... 424/450; 424/70.12
[58] Field of Search ............... 424/450, 70, 455, 424/462, 70.12

[56] References Cited

U.S. PATENT DOCUMENTS

| | | | |
|---|---|---|---|
| 4,876,039 | 10/1989 | Lo et al. | 424/462 |
| 5,055,228 | 10/1991 | Zabotto et al. | 424/450 |
| 5,130,171 | 7/1992 | Prud'Homme | 424/462 |
| 5,154,930 | 10/1992 | Popescu | 424/455 |

FOREIGN PATENT DOCUMENTS

| | | |
|---|---|---|
| 0043327 | 1/1982 | European Pat. Off. . |
| 0155806 | 9/1985 | European Pat. Off. . |
| 2315991 | 1/1977 | France . |
| 2597345 | 10/1987 | France . |
| 2597367 | 10/1987 | France . |
| 1539625 | 1/1979 | United Kingdom . |
| 2198947 | 6/1988 | United Kingdom . |
| 2199494 | 7/1988 | United Kingdom . |

*Primary Examiner*—Sallie M. Gardner
*Attorney, Agent, or Firm*—Cushman, Darby & Cushman Intellectual Property Group of Pillsbury Madison & Sutro, LLP

[57] ABSTRACT

The invention relates to a process for manufacturing a cosmetics composition for application to hair, which contains at least one lipid, at least one silicone and water, characterized in that at least one ionic amphiphilic lipid capable of forming vesicles with at least one silicone is mixed with water, in that this mixture is subjected to a process for forming vesicles which encapsulate an aqueous phase, and in that a dispersion of the product obtained is carried out in an aqueous dispersion phase. The invention also relates to a composition obtained by the process and to a process for cosmetic treatment of hair by means of the said composition.

23 Claims, No Drawings

PROCESS FOR MANUFACTURING A COSMETICS COMPOSITION FOR APPLICATION TO HAIR, COMPOSITION OBTAINED BY THIS PROCESS AND PROCESS FOR COSMETIC TREATMENT USING THE SAID COMPOSITION

The present invention relates to a process for manufacturing a cosmetic composition for application to the hair, the cosmetic composition obtained by this process and a process for cosmetic treatment using the said composition.

It is well known that hair is sensitized or weakened to various degrees by the action of atmospheric agents and/or of certain cosmetic treatments, such as permanent waves, dyeings or bleachings. Sensitized or weakened hair becomes difficult to disentangle and to style either in the wet state or in the dry state. Furthermore, it feels rough, no longer has a sleek or lustrous appearance and is charged with static electricity.

The application to hair of compositions which allow these varied problems to be remedied has thus been sought.

The use of oils and of fats to give the hair back its softness and lustre has been known for a very long time; the application of these compounds is generally followed by shampooing in order to remove the excess oil or fat from the hair. However, the use of oils and fats makes the hair weaker and heavier and it is impossible to afterwards obtain a styling which has firmness and body.

It has already been proposed to use compositions containing silicone oils. These make it possible to obtain lustrous hair but their prolonged use or use in large quantities has the disadvantage of giving a greasy appearance to hair.

Aqueous compositions containing cationic surface-active agents are commonly used which are applied to the hair and which are left to act for several minutes before the hair is rinsed. Cationic surface-active agents improve disentangling and styling, but have disadvantages: they have a tendency to make the hair heavy and to give it a greasy appearance. Furthermore, the hair has a tendency to rapidly get dirty again. These disadvantages are more marked as the treated hair becomes finer and more sensitive.

The use is also known of compositions containing both cationic surface-active agents and oils or glycerides. These compositions can have good cosmetic and rheological properties but they have a tendency to form a deposit on the hair.

Moreover, it is known that certain amphiphilic lipids are capable of forming, by stirring in the presence of an aqueous phase, a hydrated lipid lamellar phase which leads to vesicles; French Patent No. 2,315,991 describes, in particular, the case where the amphiphilic lipid is an ionic lipid. These vesicles consist of one or more concentric layers (bimolecular or multimolecular layers of lipids encapsulating an internal aqueous phase). The ionic lipid(s) used is (are), in a known way, amphiphilic lipids of natural or synthetic origin containing, per molecule, one (or more) long hydrocarbon chain(s). The many processes for manufacturing ionic lipid vesicles are well known. In a first type of process (see particularly U.S. Pat. No. 4,772,471), the amphiphilic lipids are dissolved in a solvent and then the solvent is evaporated; the aqueous phase to be encapsulated is then introduced with stirring and the whole is subjected to vigorous stirring. In a second type of process (see particularly FR-A-2,315,991), the use of a solvent is avoided: in a first stage, molten (70°–95° C., for example) ionic amphiphilic lipid(s) is (are) brought into contact with the aqueous phase to be encapsulated with vigorous stirring until vesicles are formed; in a second stage, an aqueous dispersion phase, which is identical to or different from the aqueous phase to be encapsulated, is added while continuing stirring.

In a third type of process (see particularly FR 89 13358), the ionic amphiphilic lipid(s) is (are) dissolved in a water-immiscible organic solvent; the organic phase thus obtained is added to an aqueous phase in quantities such that, with vigorous stirring, a dispersion of the oil-in-water type is obtained; the solvent is evaporated with vigorous stirring, the continuous phase of the dispersion always being the aqueous phase, it being possible for the dispersion then to be optionally concentrated.

According to the present application, it has been found that the treatment characteristics of hair using an aqueous composition containing silicones and lipids are improved when ionic amphiphilic lipids capable of forming vesicles are used as lipids and when the composition is prepared using a known process for manufacturing ionic vesicles, in which the ionic amphiphilic lipid and the silicone are mixed before the process of formation of the vesicles.

It has been verified, in particular by electron microscopy, that the composition thus prepared contains stable vesicles.

It has been shown, by comparative trials, that the fact of introducing the silicone into the ionic amphiphilic lipid before the process of formation of the vesicles makes it possible to obtain better results than when the silicone is introduced into the aqueous dispersion phase for the vesicles after formation of the latter.

The first subject of the present invention is thus a process for manufacturing a cosmetic composition for application to hair, which contains at least one lipid, at least one silicone and water, characterized in that at least one ionic amphiphilic lipid capable of forming vesicles with at least one silicone is mixed with water, in that this mixture is subjected to a process for forming vesicles encapsulating an aqueous phase and in that a dispersion of the product obtained is carried out in an aqueous dispersion phase.

Preferably, the aqueous dispersion phase contains at least one cationic surface-active agent.

The process for forming vesicles used is, preferably, a process which does not require a solvent, in which the mixture of ionic amphiphilic lipid(s) and silicone(s) is melted, an aqueous phase to be encapsulated is introduced so as to form a hydrated lamellar phase, the addition of this phase is continued with vigorous stirring in order to form vesicles and then an aqueous dispersion phase is added.

It is also possible to use a process in which the ionic amphiphilic lipid(s) and the silicone(s) are dissolved in an organic solvent; in the container where the solution thus obtained is placed, the solvent is evaporated in order to form, on the walls of the said container, a film of the (lipid(s)/silicone(s)) mixture; the aqueous phase to be encapsulated is added, with vigorous stirring, into the said container until the vesicles have formed; finally, an aqueous dispersion phase is added.

The ionic amphiphilic lipid used according to the present invention is advantageously chosen from the following compounds:

a) natural or synthetic phospholipids, particularly egg or soya lecithin, sphingomyelin, dipalmitoyl phosphatidylcholine or hydrogenated lecithin;

b) amphoteric compounds containing two lipophilic chains or a combination of two long-chain organic ions with opposite signs;

c) anionic compounds.

Among the anionic compounds, those chosen advantageously are of formula:

$$R_1-CHOH-CH-COA$$
$$|$$
$$R_2-CONH$$

in which formula:

$R_1$ denotes a $C_7-C_{21}$ alkenyl or alkyl radical;

$R_2$ denotes a $C_7-C_{31}$, saturated or unsaturated hydrocarbon radical;

COA denotes a group chosen from the following groups: COOM, M being H, Na, K, NH$_4$ or a substituted ammonium ion derived from an amine; residue $$CON-B$$
$$|$$
$$R_3$$

B being a radical derived from mono- or polyhydroxylated primary or secondary amines and $R_3$ denoting a hydrogen atom or a methyl, ethyl or hydroxyethyl radical;

a residue $$-CON-Q$$
$$|$$
$$R_3$$

Q denoting a substituted aminoalkyl or ammonioalkyl radical and $R_3$ having the meaning indicated above; and COOZ, Z representing the residue of a $C_3-C_7$ polyol.

In a known way, these ionic lipids can be combined with at least one stabilizing additive intended to modify the permeability or the surface charge of the lipid layers of the hydrated lipid lamellar phase. According to the invention, these additives are more particularly chosen from the group formed by sterols, such as cholesterol or betasitosterol; monosodium or disodium salts of acylglutamates, the acyl radical being $C_{14}-C_{22}$, such as the monosodium salt of stearoylglutamate, the disodium salts of glutamates of cocoyl- and stearoylglutamates or glutamates of mixtures of acyl radicals derived from copra and tallow, phosphoric esters of $C_{12}-C_{16}$ fatty alcohols and lipophilic surfactants, such as oxyethylenated phyosterols.

The anionic stabilizing agents are combined with the ionic amphiphilic lipid compounds in a quantity which does not, preferably, exceed 12% by weight in relation to the weight of the ionic amphiphilic lipid(s) which constitute(s) the hydrated lipid lamellar phase. However, for sterols and especially cholesterol, this same proportion can range up to 100% by weight.

The silicone(s) mixed with the ionic amphiphilic lipids, according to the present invention, is (are) advantageously chosen from the:

polydimethylsiloxanes and their mixtures with a trimethylsiloxysilicate;

polydimethylsiloxanes modified with hydroxyl groups at the chain ends;

polydimethylsiloxanes modified with $C_{12}-C_{22}$ alkoxy groups;

polydimethylsiloxanes modified with polyoxyalkylenated groups, the alkylene radical being $C_2$ or $C_3$;

polydimethylsiloxanes modified with acyloxyalkyl radicals in which the acyl radical is $C_{12}-C_{22}$ and the alkyl radical is $C_1-C_4$;

polymethylphenylsiloxanes, polymethyl ($C_1-C_{20}$) alkylsiloxanes;

polymethyl[($C_1-C_4$) alkylaryl]siloxanes modified with ($C_1-C_4$) alkylamine groups; and cyclopolysiloxanes.

Among the silicones advantageously used, there may be mentioned those sold under the following trade names:

"Silbione 47V500000" by the company "Rhone-Poulenc" (polydimethylsiloxane having a molecular weight of approximately 250,000);

"Fluid Dow Corning 593" by the company "Dow Corning" or "SS 4267 Silicone Fluid" sold by the company "General Electric Corp." (mixture of polydimethylsiloxane and trimethylsiloxysilicate);

"Silicone Copolymer F 555" by the company "S.W.S. Silicones Corp." (stearoxypolydimethylsiloxane);

"Rhodorsil Huile 70633V30" by the company "Rhone-Poulenc" (polymethylphenylsiloxane);

"GP 7100 Silicone Fluid" by the company "Genesee Polymers Corp." (polymethyl(alkylaryl)siloxane modified with alkylamine groups);

"Volatile Silicone FZ 3109" sold by the company "Union Carbide" (tetramethyltetraoctylcyclotetrasiloxane).

The silicones used can be in the form of oils, gums or water-insoluble resins, volatile or otherwise.

At least one nonvolatile silicone is preferably used, such as a chain end-hydroxylated polydimethylsiloxane oil or a polyphenylmethylsiloxane gum, in the form of a solution in at least one cyclic volatile silicone oil of the cyclomethicone type.

More particularly, the following solutions are used:

15% by weight of a nonvolatile polydimethylsiloxane such as that sold under the trade name "Silbione 47V500000" by the company "Rhone-Poulenc" in solution in 85% by weight of decamethylcyclopentasiloxane such as that sold under the trade name "Volatile Silicone 7158" by the company "Union Carbide";

13% by weight of a mixture of chain end-hydroxylated, nonvolatile polydimethylsiloxanes such as that sold under the trade name "Q2 1401" by the company "Dow Corning" in solution in 87% by weight of a mixture of decamethylcyclopentasiloxane and octamethylcyclotetrasiloxane;

15% by weight of a nonvolatile phenylmethylsiloxane gum having a molecular weight of approximately 600,000 in solution in 85% by weight of a mixture of decamethylcyclopentasiloxane and octamethylcyclotetrasiloxane.

The cationic surface-active agent optionally contained according to the invention in the aqueous dispersion phase is generally dispersed while warm in water. This phase is then mixed with the dispersion principally containing the ionic lipid and the silicone. The mixing is carried out either while warm or at room temperature. The surface-active agent is advantageously a surface-active agent which is insoluble in water at room temperature. It is, preferably, at least one quaternary ammonium derivative of formula II:

$$\begin{array}{c} R_5 \quad\quad R_8 \\ \diagdown \overset{\oplus}{N} \diagup \quad X^{\ominus} \\ \diagup \quad \diagdown \\ R_6 \quad\quad R_7 \end{array} \quad\quad (II)$$

in which formula X is chlorine or $CH_3SO_4$ and $R_5$ is a $C_1-C_4$ alkyl radical, preferably the methyl radical, and in which:

either $R_6$ and $R_7$ are $C_1-C_4$ alkyl radicals, which are identical to or different from $R_5$ and each other, and $R_8$ is a $C_{20}-C_{22}$ alkyl radical;

or $R_6=R_5$ and $R_7=R_8=C_{18}$ alkyl radical;

or $R_6$ denotes an (alkyl and/or alkenyl)amidoethyl radical in which the alkyl and/or alkenyl radical is $C_{13}$–$C_{21}$ and derives from the fatty acids of tallow and $R_7$ and $R_8$ together with the nitrogen form a 4,5-dihydroimidazole heterocycle which is substituted, particularly at the 2-position, with a $C_{13}$–$C_{21}$ alkyl and/or alkenyl radical.

The surface-active agent is more particularly a tetraalkylammonium chloride of formula (II), in which $R_5$, $R_6$ and $R_7$ are identical, $C_1$–$C_4$ alkyl radicals, preferably methyl, and $R_8$ is a $C_{20}$–$C_{22}$ alkyl radical. Behenyltrimethylammonium chloride can be advantageously used.

It is also possible to advantageously use distearyldimethylammonium chloride, the compound of formula (II) in which $R_5=R_6=CH_3$ and $R_7=R_8=C_{18}$ alkyl.

When the surface-active agent is a methyl sulphate, it is advantageously the compound of formula III:

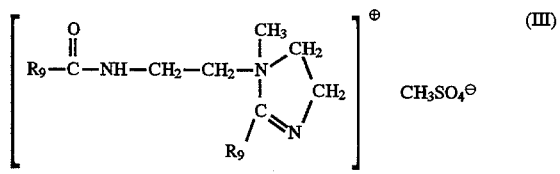

in which $R_9$ denotes a mixture of $C_{13}$–$C_{21}$ alkenyl and/or alkyl radicals derived from the fatty acids of tallow, for example the products sold under the trade names "Rewoquat (W 75, W 75 PG, W 90, W 90 DPG, W 1599, W 75 H)" by the company "Rewo".

According to the present invention, it is possible in a known way to add to the ionic amphiphilic lipid(s) and/or to the silicone(s), before the formation of vesicles, at least one liposoluble cosmetic and/or pharmaceutical active principle which will be in the lipid layers of the vesicles. It is also possible to introduce, into the aqueous phase to be encapsulated and/or into the aqueous dispersion phase, at least one water-soluble cosmetic and/or pharmaceutical active principle. Among the active principles, there may be mentioned vitamin A acid, linoleic acid, the tocopherols and the agents which act against hair loss or for hair regrowth, antidandruff agents, retinoids or related compounds, anti-inflammatories, antifungal agents, antiseborrheic agents, and sunscreens or the like.

Among the additives there may be mentioned preserving agents, coloring agents, fragrances or the like. In particular it is possible to introduce, in a known way, a thickening agent into the aqueous dispersion phase. The thickening agents are more particularly chosen from the cellulose derivatives such as hydroxymethylcellulose, carboxymethylcellulose, hydroxybutylcellulose, hydroxypropylcellulose and more particularly hydroxyethylcellulose, such as the products sold under the trade name "Natrosol" (150, 250) by the company "Hercules" or "Cellosize" (QP and WP) by the company "Union Carbide" or "Natrosol Plus Grade 330 CS" by the company "Aqualon", methyl-hydroxypropylcellulose, in particular the products sold under the name "Methocel" (E, F, J, K) by the company "Dow Chemical" or the heterobiopolysaccharides such as, for example, the xanthan gums marketed under the names "Keltrol" and "Kelzan" by the company "Kelco", "Rhodopol" and "Rhodigel" by the company "Rhone-Poulenc" or "Actigum" by the company "Ceca/ Satia".

These thickening agents can be, according to the invention, incorporated without distinction in compositions optionally containing a cationic surfactant.

When the compositions do not contain a cationic surfactant, it is also possible to use as thickening agent crosslinked polyacrylic acids such as the products sold under the trade name "Carbopol" by the company "Goodrich", such as "Carbopol 910, 934, 934P, 940, 941, 1342".

It is also possible to introduce, in a known way, a water-immiscible substance such as an oil into the aqueous dispersion phase.

A second subject of the present invention is a composition obtained by the process defined above, comprising at least one silicone and at least one ionic amphiphilic lipid in the form of vesicles dispersed in an aqueous dispersion phase; this composition also contains, preferably, at least one cationic surfactant.

The composition according to the invention advantageously contains, calculated by weight in relation to the total weight of the composition:

1 to 10% of cationic surface-active agent(s);

1.5 to 20% of ionic amphiphilic lipid(s);

0.5 to 10% of silicone(s); and, preferably:

1 to 7% of surface-active agent(s);

1.5 to 10% of ionic amphiphilic lipid(s);

1.5 to 5% of silicone(s).

The composition according to the invention is in a cream or lotion form.

The compositions according to the invention are used, preferably, in the form of products to be rinsed, before and more particularly after a shampooing, before and more particularly after a dyeing or a bleaching, before and more particularly after a permanent wave or a hair straightening. These compositions have been found to be stable over time, even in the presence of cationic surface-active agents, which was not foreseeable at all by those skilled in the art, particularly in view of the indications contained in the patent U.S. Pat. No. 3,957,971 (column 11, line 1). Moreover, these compositions exhibit an array of cosmetic properties which have advantages over the prior art, and are all the more advantageous and surprising because their effect is immediate, that is to say that it is not necessary for the user to leave the composition in place before rinsing, which results in a very appreciable gain in time and a more convenient use. Nevertheless, it remains possible to leave the composition for some time before rinsing, without this altering the good properties obtained.

These compositions do not make the hair greasy, do not weaken it, disentangle it easily and allow an easy combing in the damp or dry state.

The said compositions additionally confer surprising properties on the hair, such as a uniform sleekness, a lightness and a high softness from the root to the tip. A surprising effect of individualization of the hair fibres and a significant reduction in the static electricity are found. These properties are obtained on normal or not greatly sensitized hair when the composition does not contain a cationic surface-active agent and also on sensitized hair when the composition contains a cationic surface-active agent.

These compositions are also removed very easily by rinsing with water.

The third subject of the present invention is a process for cosmetic treatment of the hair, characterized in that an effective quantity of the composition according to the invention is applied to the latter, in that optionally the hair is combed and in that finally the said hair is rinsed.

According to this treatment, quantities of composition, in general, of the order of 5 to 40 g per head are applied.

The examples given below, as illustrative and nonlimiting, make it possible to better understand the invention.

EXAMPLE 1

In a first stage, a constituent (A) containing vesicles is prepared. 5 g of soya lecithin are mixed, while stirring gently at a temperature of 60° C., with 75% of phosphatidylcholine, sold by the company "Seppic" under the name "Lipoid S 75", and 3 g of a chain end-hydroxylated polydimethylsiloxane (MW=600,000) (15%) combined with a mixture (50/50) of octamethylcyclotetrasiloxane and decamethylcyclopentasiloxane (85%) and mixing is continued until perfectly homogeneous (5 min).

16 g of water, brought to 80° C. and containing a preserving agent, are introduced into the molten mixture and mixing is carried out for approximately 5 min; the mixture is left to swell for 1 hour. 24 g of water at 20° C. are added to the phase thus obtained; the mixture is stirred for a few minutes; the mixture is then fined by passing at 500 bars into a "Rannie"-type homogenizer. Preparation is completed with 11.6 g of water at 20° C., with stirring.

In a second stage, a constituent (B) containing the aqueous dispersion phase is prepared: 1.5 g of distearyldimethylammonium chloride are dissolved at 80° C. in 38.2 g of water for 10 minutes. The solution is left to cool to 50° C.

Mixing of constituent (A) and constituent (B) is carried out and the mixture is homogenized with gentle stirring. When the temperature reaches approximately 40° C., the fragrance and a preserving agent are added, the weight is made up to 100 g with water at room temperature and the mixture is gently stirred until it has returned to room temperature.

A composition is obtained which is stable over time.

This composition is applied in an amount of approximately 12 g onto sensitized hair which has been washed and towel-dried. The hair is rinsed copiously with water. The damp hairs disentangle easily, and are smooth and soft from the root to the tip. After drying, they are lively, they comb very easily and they are not electric; they are lustrous, sleek and free from tangling over their whole length. The styling is light and bouffant.

EXAMPLE 2

In a first stage, a constituent (A) comprising vesicles is prepared. A mixture of 1.75 g of soya phospholipids sold by the company "Nattermann" under the name "Phospholipon 80" and 2 g of a mixture of 15% by weight of polyphenylmethylsiloxane (MW=600,000) in 85% by weight of a mixture (50/50) of octamethylcyclotetrasiloxane and decamethylcyclopentasiloxane is mixed while gently stirring at a temperature of 60° C. and this is continued until perfectly homogeneous (5 min).

7.5 g of water, brought to 80° C. and containing a preserving agent, are introduced into the molten mixture and mixing is carried out for approximately 5 min; the mixture is then left to swell for 1 hour. 11.25 g of water at 20° C. are added to the phase thus obtained; the mixture is stirred for a few minutes; the mixture is then fined by passing at 500 bars into a "Rannie"-type homogenizer. Preparation is completed with 37 g of water at 20° C., with stirring.

In a second stage, a constituent (B) containing the aqueous dispersion phase is prepared: 2.8 g of behenyltrimethylammonium chloride, containing 80% of active substance in a water/isopropanol (15/85) mixture, are dissolved at 80° C. in 30 g of water for 10 minutes. The solution is left to cool to 50° C.

Mixing of constituent (A) and constituent (B) is carried out and the mixture is homogenized with gentle stirring. When the temperature reaches approximately 40° C., the fragrance and a preserving agent are added and the weight is made up to 100 g with water at room temperature while gently stirring until the mixture has returned to room temperature.

A stable composition is obtained which has the same cosmetic properties on hair as the composition of Example 1.

EXAMPLE 3

In a first stage, a constituent (A) comprising vesicles is prepared. 0.92 g of phytosterol polyoxyethylenated with 5 mol of ethylene oxide, sold by the company "Nikko" under the name "Generol 122 E 5", is melted while stirring gently at a temperature of 85° C. A mixture of 1.38 g of hydrogenated lecithin containing 30–35% of hydrogenated phosphatidylcholine, sold by the company "Nikko" under the name "Lecinol S 10", with 0.75 g of a polydimethylsiloxane, sold under the name "Silbione 47 V 500000" by the company "Rhone-Poulenc", and 4.25 g of decamethylcyclopentasiloxane, is then added to the molten mixture, until perfectly homogenous (5 min).

14.6 g of water, brought to 80° C. and containing a preserving agent, are introduced into the molten mixture and mixing is carried out for approximately 5 min; the mixture is then left to swell for 1 hour. 21.9 g of water at 20° C. are added to the phase thus obtained; the mixture is stirred for a few minutes; the mixture is fined by passing at 500 bars into a "Gaulin"-type homogenizer; the preparation is then completed with 16.45 g of water at 20° C., with stirring.

In a second stage, a constituent (B) containing the aqueous dispersion phase is prepared: 5 g (as active substance) of a quaternary ammonium salt (in solution in propylene glycol at approximately 75% active material), sold by the company "Rewo" under the trade name "Rewoquat W 75 PG", are dissolved at 80° C. in 18 g of water for 10 minutes. The solution is left to cool to 50° C.

Mixing of constituent (A) and constituent (B) is carried out and the mixture is homogenized with gentle stirring. When the temperature reaches approximately 40° C., the fragrance and a highly homogenous aqueous gel consisting of 0.25 g of hydroxyethylcellulose, sold under the name "Natrosol Plus Grade 330 CS" by the company "Aqualon", dissolved in 15 g of water containing a preserving agent, are added; the weight is then made up to 100 g with water at room temperature and the mixture is gently stirred until it has returned to room temperature.

A stable composition is obtained which has the same cosmetic properties on hair as the composition of Example 1.

EXAMPLE 4

In this example, the activity of two aqueous compositions A and B containing the same quantities of the same lipid, silicone and cationic surface-active constituents was compared:

- a composition A, in accordance with the invention, for which the silicone was mixed with the ionic amphiphilic lipid before the formation of vesicles:
- a composition B, not in accordance with the invention, in which the silicone was introduced into the dispersion phase.

The compositions A and B correspond to the following formulation, given by weight;

Phytosterol polyoxyethylenated with 5 mol of ethylene oxide, sold under the name "Generol 122 E 5" by the company "Nikko" . . . 0.92 g Hydrogenated lecithin containing 30 to 35% hydrogenated phosphatidylcholine, sold under the name "Lecinol S10" by the company "Nikko" ... 1.38 g Silicone sold under the name "Q2-1401" by the company "Dow Corning ... 2.90 g Cationic surfactant of formula (III), sold under the name "Rewoquat W75 PG" by the company "Rewo" (as weight of active material) ... 2.00 g

| Preserving agent | qs | |
|---|---|---|
| Water | qs | 100.00 g |

The compositions A and B were applied simultaneously in an amount of 6 g per half-head on sensitized hair which had been washed and towel-dried. The whole hair is copiously rinsed, combed and dried.

It was found that, after application, the distribution of composition A is better and that, once dried, hair treated with composition A according to the invention exhibits superior cosmetic properties as regards body, liveliness and lightness.

EXAMPLE 5

In this example, the activity of two aqueous compositions C and D containing the same quantities of the same lipid and silicone constituents was compared:

a composition C, in accordance with the invention, for which the silicone was mixed with the ionic amphiphilic lipid before the formation of vesicles:

a composition D, not in accordance with the invention, in which the silicone was introduced into the dispersion phase.

The compositions C and D correspond to the following formulation, given by weight;

Phytosterol polyoxyethylenated with 5 mol of ethylene oxide, sold under the name "Generol 122 E 5" by the company "Nikko" ... 3.0 g Hydrogenated lecithin containing 30 to 35% hydrogenated phosphatidylcholine, sold under the name "Lecinol S10" by the company "Nikko" ... 4 5 g Silicone sold under the name "Q2-1401" by the company "Dow Corning ... 4.0 g

| Preserving agent | qs | |
|---|---|---|
| Water | qs | 100.00 g |

The compositions C and D were applied simultaneously in an amount of 6 per half-head on sensitized hair which had e washed and wrung. The whole hair is copiously rinsed, combed and dried.

It was found that, after application, the hair treated with composition C is sleeker and lighter; that rinsing of hairs treated with composition C is easier and that, once dried, hairs treated with composition C are more lustrous, have more body and are less entangled over their whole length than with composition D.

I claim:

1. A process for manufacturing a cosmetic composition for application to the hair, said process comprising (a) admixing at least one ionic amphiphilic lipid capable of forming vesicles with at least one silicone, (b) mixing the mixture resulting from (a) with an aqueous phase to be encapsulated in said vesicles so as to form a hydrated lamellar phase, (c) forming said vesicles from said hydrated lamellar phase resulting from (b) and (d) dispersing the vesicles resulting from (c) in an aqueous dispersion phase.

2. The process of claim 1 wherein said aqueous dispersion phase contains at least one cationic surface-active agent.

3. The process of claim 1 wherein said step (a) comprises melting said ionic amphiphilic lipid and said silicone and step (b) comprises introducing said aqueous phase to be encapsulated with the molten mixture resulting from step (a) and stirring the resulting mixture so as to form said vesicles and thereafter adding said aqueous dispersion phase to the resulting vesicles.

4. The process of claim 1 wherein said ionic amphiphilic lipid and said silicone in step (a) are dissolved in an organic solvent in a container, evaporating the said solvent and adding to said container the said aqueous phase to be encapsulated with stirring until said vesicles are formed and thereafter adding said aqueous dispersion phase.

5. The process of claim 1 comprising (a) in a first stage dissolving at least one ionic amphiphilic lipid capable of forming vesicles and at least one silicone in at least one water-immiscible organic solvent so as to form an organic phase;

(b) in a second stage adding the said organic phase resulting from said first stage to an aqueous phase in an amount such that the dispersion obtained in a subsequent stage is an oil-in-water dispersion;

(c) in a third stage, dispersing the mixture resulting from said second stage by stirring said mixture;

(d) in a fourth stage, evaporating said water-immiscible organic solvent together with a part of the water of said aqueous phase so that the continuous phase of the said dispersion is an aqueous phase.

6. The process of claim 1 wherein said ionic amphiphilic lipid is selected from the group consisting of:

(a) a natural or synthetic phospholipid;

(b) an amphoteric compound containing two lipophilic chains or a combination of two long-chain organic ions having opposite signs; and (c) an anionic compound.

7. The process of claim 1 wherein said phospholipid is egg lecithin, soya lecithin, sphingomyelin, dipalmitoyl phosphatidylcholine or hydrogenated lecithin.

8. The process of claim 1 wherein said ionic amphiphilic lipid has the formula

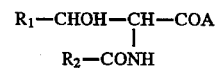

wherein $R_1$ represents a $C_7$–$C_{21}$ alkenyl or alkyl radical, $R_2$ represents a saturated or unsaturated $C_7$–$C_{31}$ hydrocarbon radical, —COA represents a member selected from the group consisting of:

(a) —COOM wherein M is H, Na, K, $NH_4$ or a substituted ammonium ion derived from an amine, (b)

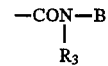

wherein B is a radical derived from a mono- or polyhydroxylated primary or secondary amine and $R_3$ represents hydrogen, methyl, ethyl or hydroxyethyl, (c)

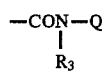

wherein Q represents a substituted amino alkyl or ammonio alkyl radical and $R_3$ has the meaning given above, and (d) —COOZ wherein Z represents the residue of a $C_3$–$C_7$ polyol.

9. The process of claim 1 which includes combining said ionic amphiphilic lipid with at least one stabilizing additive so as to alter the permeability or the surface charge of said hydrated lamellar phase.

10. The process of claim 9 wherein said stabilizing additive is selected from the group consisting of a sterol; a monosodium or disodium salt of an acylglutamate wherein the acyl moiety has 14–22 carbon atoms; a phosphoric ester of a $C_{12}$–$C_{16}$ fatty-alcohol; and a lipophilic surfactant.

11. The process of claim 9 wherein said stabilizing additive is added in an amount less than 12 percent by weight relative to the weight of said ionic amphiphilic lipid.

12. The process of claim 10 wherein said stabilizing additive is a sterol present in an amount which is less than 100 percent by weight relative to the weight of said ionic amphiphilic lipid.

13. The process of claim 1 wherein said silicone is at least one nonvolatile silicone in solution in at least one cyclic volatile silicone oil.

14. The process of claim 2 wherein said surface-active agent is at least one quaternary ammonium derivative of formula II:

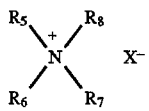

wherein

X is chlorine or $CH_3 SO_4$ and $R_5$ is $C_1$–$C_4$ alkyl and wherein either $R_6$ and $R_7$ are $C_1$–$C_4$ alkyl which are identical to or different from $R_5$ and each other, and $R_8$ is a $C_{20}$–$C_{22}$ alkyl radical;

or $R_6=R_5$ and $R_7=R_8=C_{18}$ alkyl radical;

or $R_6$ represents an (alkyl, or alkenyl or both) aminoethyl radical in which the alkyl and alkenyl moieties contain 13–21 carbon atoms derived from the fatty acids of tallow and $R_7$ and $R_8$ together with the nitrogen atom to which they are attached form a 4,5-dihydroimidazole heterocycle substituted with a $C_{13}$–$C_{21}$ alkyl or a $C_{13}$–$C_{21}$ alkenyl radical or both.

15. The process of claim 1 which includes adding at least one liposoluble pharmaceutical or cosmetic active principle, or both, to said ionic amphiphilic lipid or to said silicone or to both.

16. The process according to claim 1 which includes adding at least one water-soluble cosmetic or pharmaceutical active principle, or both, to said aqueous phase to be encapsulated in said vesicles or to said aqueous dispersion phase, or both.

17. The process of claim 1 which includes adding a water-immiscible oil to said aqueous dispersion phase.

18. A composition obtained by the process of claim 1 comprising at least one silicone and at least one ionic amphiphilic lipid in the form of vesicles dispersed in an aqueous dispersion phase.

19. The composition of claim 18 wherein said aqueous dispersion phase contains at least one cationic surface-active agent.

20. The composition of claim 19 containing, calculated by weight relative to the total weight of said composition, 1 to 10 percent of a cationic surface-active agent, 1.5 to 20 percent of an ionic amphiphilic lipid, and 0.5 to 10 percent of a silicone.

21. The composition of claim 19 containing, calculated by weight relative to the total weight of said composition, 1 to 7 percent of a cationic surface-active agent, 1.5 to 10 percent of an ionic amphiphilic lipid, and 1.5 to 5 percent of a silicone.

22. A process for the cosmetic treatment of hair comprising applying to said hair a cosmetically effective amount of the composition of claim 18, optionally combing the hair, and rinsing said hair.

23. The process of claim 1 wherein said silicone is selected from the group consisting of a polydimethylsiloxane;

a mixture of a polydimethylsiloxane and trimethylsiloxysilicate;

a polydimethylsiloxane modified with a hydroxyl group at the chain end;

a polydimethylsiloxane modified with a $C_{12}$–$C_{22}$ alkoxy group;

a polydimethylsiloxane modified with a polyoxyalkylenated group wherein the alkylene moiety has 2 or 3 carbon atoms;

a polydimethylsiloxane modified with an acyloxyalkyl radical wherein the acyl moiety has 12–22 carbon atoms and the alkyl moiety has 1–4 carbon atoms;

a polymethylphenylsiloxane;

a polymethyl ($C_1$–$C_{20}$) alkylsiloxane;

a polymethyl (($C_1$–$C_4$) alkylaryl)) siloxane modified with a ($C_1$–$C_4$) alkylamine group; and a cyclopolysiloxane.

* * * * *